(12) United States Patent
Black (10) Patent No.: US 10,371,686 B2
(45) Date of Patent: Aug. 6, 2019

(54) DETECTION DEVICE FOR MOLTEN METAL (71) Applicant: Heraeus Electro-Nite International N.V., Houthalen (BE)

(72) Inventor: Jason Black, Hasselt (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 487 days.

(21) Appl. No.: 13/677,808

(22) Filed: Nov. 15, 2012

(65) Prior Publication Data
US 2014/0134744 A1 May 15, 2014

(51) Int. Cl.
*G01N 33/20* (2019.01)
*G01N 33/205* (2019.01)
*B01L 3/04* (2006.01)
*G01N 25/04* (2006.01)
*G01N 1/12* (2006.01)

(52) U.S. Cl.
CPC .............. *G01N 33/205* (2019.01); *B01L 3/04* (2013.01); *G01N 1/125* (2013.01); *G01N 25/04* (2013.01); *B01L 2200/16* (2013.01); *Y10T 29/49* (2015.01); *Y10T 29/49002* (2015.01)

(58) Field of Classification Search
CPC .. G01N 33/206; G01N 33/4905; G01N 33/86; G01N 21/82; G01N 15/1404; G01N 33/205
See application file for complete search history.

(56) References Cited

U.S. PATENT DOCUMENTS

| 3,197,306 | A | * | 7/1965 | Osborn et al. | 420/24 |
| 3,267,732 | A | | 8/1966 | Hance | |
| 3,422,067 | A | | 1/1969 | Barton | |
| 3,546,921 | A | | 12/1970 | Bourke et al. | |

(Continued)

FOREIGN PATENT DOCUMENTS

| CN | 1240025 A | 12/1999 |
| CN | 1921969 A | 2/2007 |

(Continued)

OTHER PUBLICATIONS

Schleyer, "Refractory Specialties and the Properties of Potassium Silicates", The American Ceramic Society Bulletin, vol. 38, No. 7, pp. 341-344 (Jul. 15, 1959).
Kompatscher et al, "Efflorescence", BASF Construction Chemicals Europe AG, 28 pages (Jul. 1, 2007).
Campbell, "Elements of Metallurgy and Engineering Alloys. Chapter 24—Cast Irons", ASM International, p. 453 (Jun. 2008).
"Technical Data Sheet—Mowiol", Kuraray Europe GmbH, 4 pages (Jun. 2010).

(Continued)

*Primary Examiner* — Krishnan S Menon
*Assistant Examiner* — Dwan A Gerido
(74) *Attorney, Agent, or Firm* — Panitch Schwarze Belisario & Nadel LLP (57) ABSTRACT

A detection device for molten metal is provided. The detection device includes a sample cup having a cavity configured to receive a sample of molten metal and a blob arranged in the cavity. The blob includes a carbide stabilizing element and a hydrogen releasing material including a hydroxide of an alkaline earth metal. The blob is provided for use in detecting phase change temperatures during solidification of a sample of molten cast iron. The blob is also resistant to moisture gain and moisture loss during transport and storage. A method of detecting phase change temperatures of the molten iron or molten cast iron sample using the blob and a method of manufacturing the blob are also provided.

9 Claims, 2 Drawing Sheets

(56) References Cited

U.S. PATENT DOCUMENTS

| | | | |
|---|---|---|---|
| 3,946,594 A | | 3/1976 | Surinx |
| 4,003,425 A | | 1/1977 | Middleton |
| 4,029,140 A | | 6/1977 | Simmons |
| 4,059,996 A | * | 11/1977 | Cure ............................. 136/230 |
| 4,166,738 A | | 9/1979 | Plessers |
| 4,261,740 A | * | 4/1981 | Plessers .................. G01N 1/44 |
| | | | 266/216 |
| 4,274,284 A | | 6/1981 | Hance |
| 4,515,485 A | | 5/1985 | Cassidy et al. |
| 4,757,108 A | | 7/1988 | Walisser |
| 4,913,878 A | | 4/1990 | Dawson et al. |
| 5,496,649 A | | 3/1996 | Mallory et al. |
| 5,585,208 A | | 12/1996 | Lian et al. |
| 6,155,122 A | | 12/2000 | Junker et al. |
| 2007/0137825 A1 | * | 6/2007 | Kato et al. ........................ 164/5 |
| 2010/0000303 A1 | | 1/2010 | Kakatkar et al. |
| 2011/0014458 A1 | | 1/2011 | Stinga et al. |

FOREIGN PATENT DOCUMENTS

| | | |
|---|---|---|
| EP | 2565615 A1 | 3/2013 |
| JP | S5036199 B1 | 11/1975 |
| JP | S56162040 A | 12/1981 |
| KR | 20040010251 A | 1/2004 |

OTHER PUBLICATIONS

Extended European Search Report dated Feb. 17, 2014 in EP Application No. 13188812.5.

Search Report dated Aug. 31, 2015 in CN Application No. 2013105732853.

Office Action dated Jan. 20, 2016 in U.S. Appl. No. 14/797,413 by Black.

Office Action dated Dec. 30, 2015 in Korean Application No. 1020130135633.

* cited by examiner

DETECTION DEVICE FOR MOLTEN METAL

BACKGROUND OF THE INVENTION

The invention relates to a detection device for metal melts, in particular molten iron. The device has a sample cup and a blob containing a carbide stabilizer and a hydrogen releasing material is arranged in the sample cup.

During the processing and preparation of molten metal, particularly molten iron, it is desirous to monitor certain chemical constituents of the metal. One common means for doing so is the use of disposable phase change detection devices, which measure the temperature of a sample of the molten cast iron during solidification in order to detect the temperatures of the phase changes. Such phase change detection devices typically comprise a mold body having a cup-like shape and an upper open end for receiving a sample of molten metal. The devices also typically include a thermocouple extending into the cup below the surface of the as-poured molten metal sample. One such conventional phase change detection device is described in U.S. Pat. No. 3,267,732.

Typically, an operator scoops a sample of molten metal from a batch of the molten metal using a small spoon or ladle, and then pours the sample of molten metal into the sample mold of a detection device. The thermocouple continuously records the temperature of the metal as it solidifies. From the phase change temperature measurements of the solidifying metal sample, certain properties and aspects of the chemical composition of the cast iron sample, such as, but not limited to, carbon content, silicon content, and degree of saturation or carbon equivalent level, may be predicted. The operator can then utilize this information to make any necessary adjustments to the molten metal bath before casting.

In certain circumstances, such as for hypereutectic irons, it is useful to achieve a graphite-free, white solidification of the sampled iron. The term "white solidification" is a common term in the art and refers to an as-cast structure dominated by the solidification of iron in a carbide phase that, when fractured, appears "white."

U.S. Pat. No. 3,546,921 ("the '921 patent") teaches that the addition to the molten iron of a pellet comprising a carbide stabilizing element or compounds of such elements will promote the white solidification. However, the '921 patent does not achieve optimal white solidification because the pellet tends to rise to the surface of the molten metal as a slag, or tends to burn in atmospheric oxidation, such that it is not available for white solidification. Further, if the molten iron has a fairly high carbon content or if the molten metal has been heavily inoculated, the likelihood of achieving a total white solidification based on the pellet addition of the '921 patent is low.

U.S. Pat. No. 4,003,425 discloses that coating the inside of the sample mold with a material containing water to be liberated at the temperature of the molten iron, will improve the effectiveness of the aforementioned carbide promoting additives. In this instance, water is a vehicle whose purpose was to make available hydrogen to alloy with the metal. The improvement of an iron, especially hypereutectic irons, to solidify in a white structure is promoted by the presence of hydrogen.

U.S. Pat. No. 4,029,140 ("the '140 patent") adopts this type of coating for use in promoting the carbide reaction in a disposable sample cup. The coating contains a carbide stabilizing element or compound and a material containing loosely combined water or some hydroxyl groups. The water or hydroxyl groups are retained after drying the coating, but are freely liberated from the coating at the temperature of the molten metal.

However, the method of applying the coating of the '140 patent to such conventional disposable phase change devices was limited in its usefulness, because both the walls of the sample cup and the thermocouple itself were coated. As a result, these conventional devices suffered from a thermal lag in the thermocouple. U.S. Pat. No. 4,274,284 purports to eliminate the thermal lag by the addition of an ablative coating which ensures that the thermocouple junction is exposed to the molten metal when the sample is poured into the device.

However, the multiple coatings negated the purported economical benefit of the '140 patent. In addition, the above-described coatings were applied were to be thin, which was found to be a major drawback. Specifically, it was found that the conventional coated sample cups cannot be completely filled with molten iron due to the violent release of hydrogen from the thin coating and due to the carbide promoting material rapidly boiling away from the thin coating, rather than alloying with the metal. As such, the volume of metal remaining in the sample cup was insufficient for obtaining temperature measurements. In turn, the amount of carbide stabilizing additives to be added to the molten metal in order to effectively promote white solidification could not be reliably predicted.

Further, the carbide promoting materials and the hydrogen releasing substances of the above-described prior art coatings have melting points below that of iron and boiling points near the temperature of the phase changes that are to be monitored. Thus, even with extreme care, a reaction of the coating materials with the molten metal is to be expected, and the extent of this reaction is of importance providing a controlled alloying of the additives.

Instead of a paint or coating, U.S. Pat. No. 4,059,996 discloses a blob of material which is fixed to the bottom of the sample cup. The blob of material includes a carbide formation promoting material, a refractory material and a material for evolving hydrogen (i.e., water glass) upon contact with the molten metal. The refractory material aids in preventing the carbide formation promoting material from being burned up quickly and mixing too quickly with the molten metal. The blob is initially in the form of a fluid mixture that is deposited in the sample cup, and is then dried to a solid in an oven.

U.S. Pat. No. 4,515,485 ("the '485 patent") also discloses the use of a blob of material. However, the blob is disposed in a recess of a bottom wall of the sample cup, so that the surface area of the blob exposed to the molten metal is limited, and thus the amount of hydrated material exposed to the molten metal is limited.

None of the above-described prior art coatings and blobs satisfactorily achieves optimal white solidification for all compositions of casting irons. The reason for this failure is that each of the above-discussed prior art devices and methods fails to recognize and appreciate the problem of the environmental instability of the materials of the coatings and blobs. Specifically, the present inventors have found that the materials utilized in the above-discussed prior art coatings and blobs will, over time, lose moisture to or absorb moisture from the surrounding environment, during storage and transport to the location of use and also while awaiting use after delivery to the location of use.

For example, the prior art detection devices are provided with the coating or blob at the time of manufacturing of the device, well in advance of the time when these devices will actually be used. The manufactured devices are then boxed, palletized, shrink-wrapped and transported by land, sea or air to be unwrapped and used in another environment or location. However, during this time, the detection devices are typically subjected to uncontrolled transport and storage environments. In addition, the location at which the detection device is ultimately unwrapped and used may also be under conditions of extremes of temperature and humidity.

The present inventors have thus found that the prior art detection devices, and particularly the hydrogen releasing capacity of the coatings and blobs of these devices, are unstable because the coating or blob materials are susceptible to changes in their hydration levels. Specifically, the coatings or blobs are susceptible to taking on additional hydration in a moist environment and losing hydration in a sufficiently dry environment.

Although loss of moisture over time is problematic, the present inventors have found that exposure to damp conditions is essentially detrimental for the prior art coatings and blobs. Specifically, in damp conditions, where the prior art coatings and blobs are susceptible to uncontrolled moisture absorption from the surrounding damp environment, uncontrolled boiling of the molten metal sample results. Accordingly, as described above, the volume of metal remaining in the sample cup is insufficient for obtaining temperature measurements and, in turn, the predictability of the carbide stabilizing additives of the prior art coatings and blobs is negatively impacted.

The '485 patent recognizes that uncontrolled boiling leads to changes in the amount of molten metal remaining in the sample cup during solidification, which thus produces different results when the blobs are of a uniform size. However, this prior art device does not satisfactorily eliminate or reduce boiling. Thus, the device of the '485 patent fails to recognize the problem newly discovered by the present inventors, namely that the occurrence of uncontrolled boiling is actually the result of absorbed moisture in the carbide promoting materials. Indeed, the present inventors found that some environmentally absorbed water inevitably accumulates on even the limited exposed surface area of the blob of the '485 patent. As a result, excess boiling still occurs, thereby failing to yield the desired improvement.

Thus, the above-discussed prior art devices and methods all fail to recognize the existence of dampness and fail to address how to prevent damp conditions which occur as a result of the environmental exposure of the coatings or blobs.

BRIEF SUMMARY OF THE INVENTION

An objective of the present invention is to provide a sampling device including a blob which is capable of resisting changes in its hydrogen releasing capacity due to moisture absorption from environmental exposure during long term periods of shipping and storage.

Another objective of the present invention is to provide a sampling device in which metal samples can be obtained with optimal white solidification, while limiting the amount of hydrogen that must be added to the samples and thus limiting the violent reaction of the material directly exposed to the molten metal.

These objectives are achieved by embodiments of the present invention described and claimed in the following.

One aspect of the present invention is directed to a sampling device for molten metal. The sampling device comprises a sample cup having a cavity configured to receive a sample of molten metal and a blob arranged in the cavity. The blob comprises a carbide stabilizing element and a hydrogen releasing material including a hydroxide of an alkaline earth metal.

Another aspect of the present invention is directed to a blob for use in detecting phase change temperatures of a sample of molten iron or molten cast iron. The blob comprises a carbide stabilizing element, magnesium hydroxide as a hydrogen releasing material, a retardant which resists reaction of the blob upon contact with a sample of molten iron or molten cast iron, and a binder.

In another embodiment, the blob comprises tellurium in an amount of 15% to 60% by weight based on a total weight of the blob and magnesium hydroxide in an amount of 40% to 85% by weight based on the total weight of the blob. The blob is resistant to moisture gain and moisture loss during transport and storage.

Another aspect of the present invention is directed to a method of detecting phase change temperatures of a sample of molten iron or molten cast iron. The method comprises the steps of: providing a detection device including a temperature sensor and a sample cup with a cavity configured to receive a sample of molten iron or molten cast iron; arranging a blob in the cavity; depositing a sample of molten iron or molten cast iron into the cavity, and allowing the molten iron or molten cast iron sample to solidify while simultaneously measuring phase change temperatures of the solidifying sample. The blob comprises a carbide stabilizer and magnesium hydroxide as a hydrogen releasing material. The blob reacts upon contact with the molten iron or molten cast iron sample, such that hydrogen is released from the magnesium hydroxide into the molten iron or molten cast iron sample.

Another aspect of the present invention is directed to a method of manufacturing a blob for use in detecting phase change temperatures of a sample of molten metal. The method comprises: forming a fluid blob mixture comprising a carbide stabilizer and magnesium hydroxide as a hydrogen releasing material; providing a detection device including a sample cup with a cavity configured to receive a sample of molten metal; depositing the fluid blob mixture into the cavity; and drying the fluid blob mixture to form a blob.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

The present invention relates to a detection device for molten metals. More particularly, the present invention relates to a device for detecting and recording the temperatures of phase changes of a sample of molten iron during cooling and solidification of the molten iron. The present invention also relates to a blob of material to be attached to and positioned within the detection device.

Since the blob of material of the present invention may be applied to conventional detection devices, the structure and materials of construction of a typical detection device will be described with reference to FIGS. 1-2. However, it will be understood by those skilled in the art that the blob of material of the present invention may also be utilized with or in detection devices having other structures and materials of construction.

Figure 1:
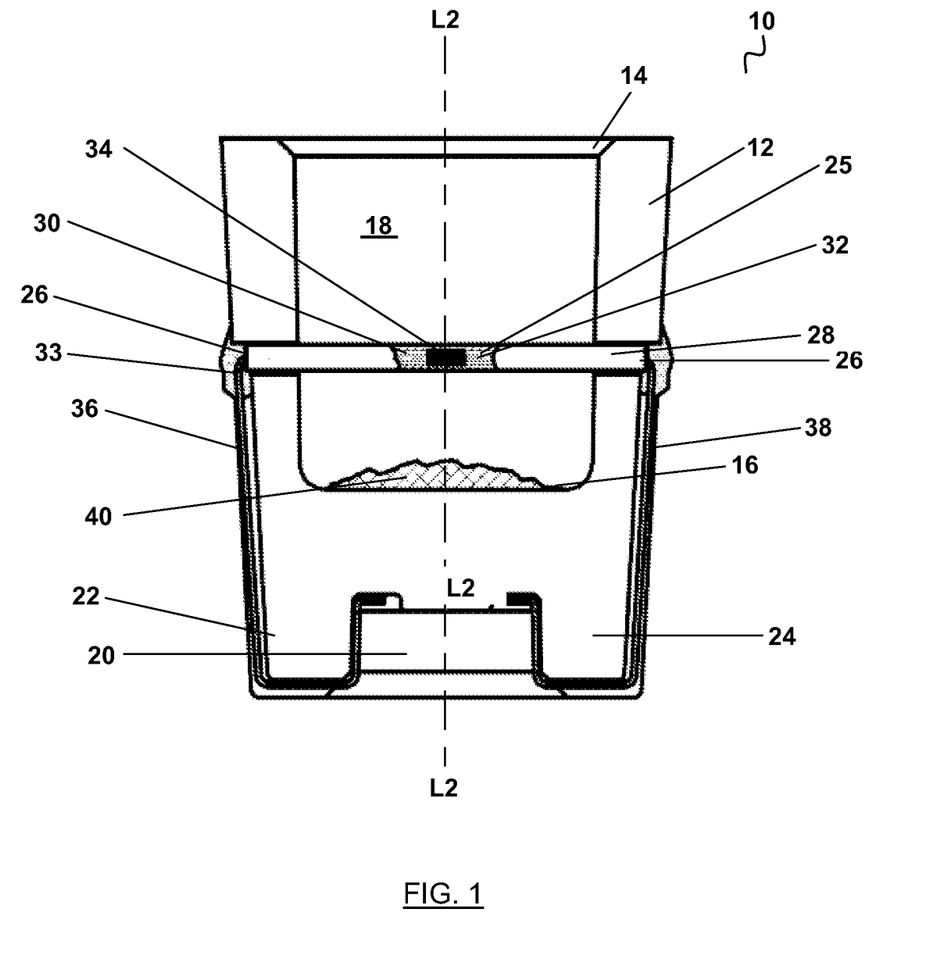
FIG. 1 is a side elevation view in cross section of a detection device according to an embodiment of the invention.
Figure 2:
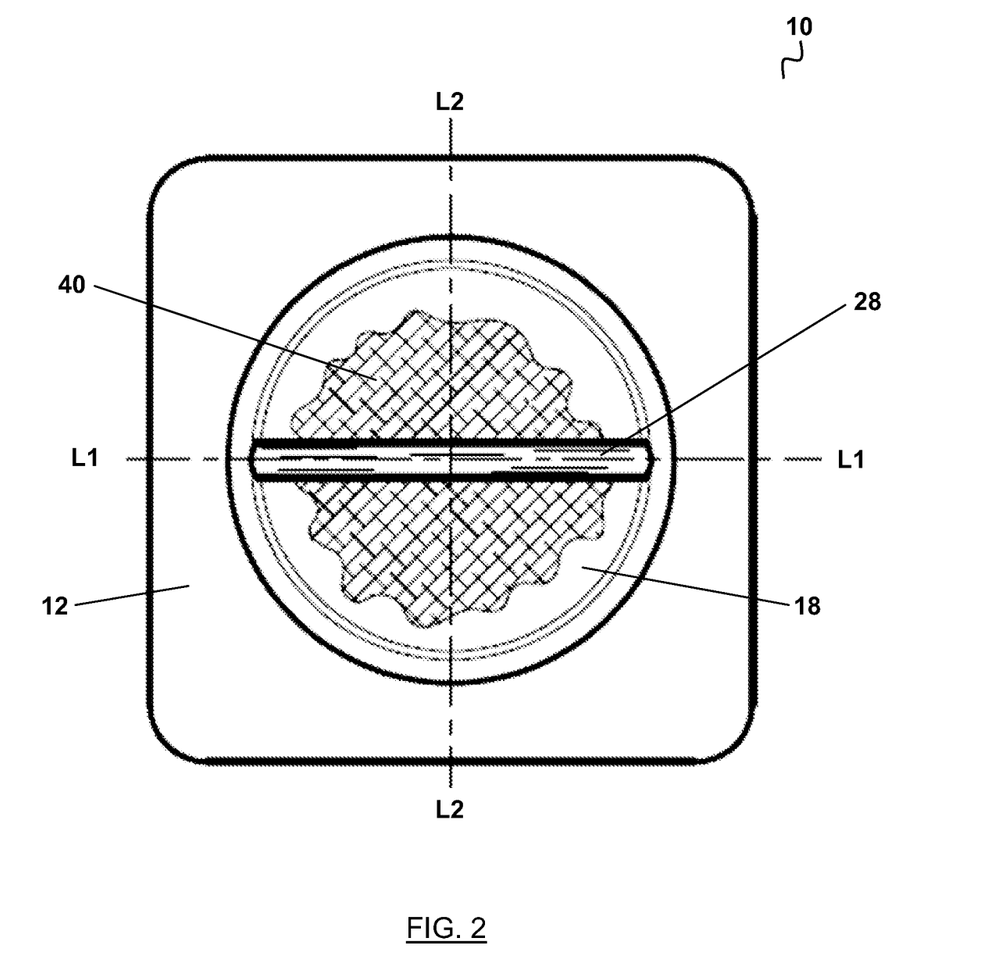
FIG. 2 is a top plan view the detection device shown in FIG. 1.

Referring to FIGS. 1-2, there is shown a detection device 10. The detection device 10 is preferably a disposable device and is used for samples of molten metal at temperatures of 1,150° C. to 1,450° C., and more preferably for samples of molten iron or molten cast iron at temperatures of 1,250° C. to 1,350° C. The detection device 10 comprises a sample chamber or cup 12 made from a refractory material. For example, the sample cup 12 may be preferably made from molded foundry sand, refractory cement, or a combination of these materials. More preferably, the sample cup 12 is made from a molded thermosetting resin coated sand. Most preferably, the sample cup 12 is made from a molded phenolic resin coated sand. However, it will be appreciated by those skilled in the art that the sample cup 12 may be made from any material capable of resisting the temperature of the molten iron and which does not adversely interfere with the desired diction and measurement.

The sample cup 12 preferably has a generally square or rectangular cross-sectional shape with an upper open end 14 and a closed bottom wall 16. A cavity 18 is formed and defined between the upper end 14 and the bottom wall 16 of the sample cup 12. The cavity 18 has a generally cylindrical configuration. The underside of the bottom wall 16 includes a centrally disposed recess 20 between opposing walls 22, 24 of the sample cup 12.

The sample cup 12 includes a temperature sensor 25 for sensing the temperature of the molten metal sample contained therein and for facilitating recording of all temperature changes. The temperature sensor includes a protective tube 28 which is preferably made of quartz. However, it will be understood by those skilled in the art that other conventional materials of a similar nature to quartz may alternatively be utilized. The protective tube 28 is preferably annular in cross section and transparent to radiation.

Thermocouple wires 30, 32 are at least partially disposed within the protective tube 28. The protective tube 28 extends across the cavity 18 and its ends are supported by first and second aligned bores 26 formed in oppositely disposed walls of the sample cup 12. The bores 26 are substantially closed with a refractory cement 33 that seals the bores 26 and maintains the position of the temperature sensor. The bores 26 are preferably provided in a location so that their axis will lie along a central lateral axis L1 of the cavity 18.

The thermocouple wires 30, 32 of the temperature sensor may be any one of the conventional thermocouple materials utilized heretofore in connection with disposable thermocouples, such as chromel and alumel, which are used with hypereutectic cast iron samples (i.e., a Type K thermocouple). Juxtaposed ends of the thermocouple wires 30, 32 are joined together at a hot junction 34. The hot junction 34 is preferably positioned adjacent to a central elevation axis L2 of the cavity 18.

Opposite walls 22, 24 of the sample cup 12 are provided with peripheral, vertically-extending grooves 36, 38. The first thermocouple wire 30 extends through and along the first groove 36 and is bent along wall 22 toward the recess 20 where it may be utilized as a contact portion for a temperature measurement recordation device (see FIG. 1). The second thermocouple wire 32 extends along and through the second groove 38 and is bent along wall 24 toward the recess 20 where it may be utilized as another contact portion (see FIG. 1). In one embodiment, the first and/or second thermocouple wire 30, 32 is preferably provided with an insulating sleeve (not shown) between the bore 26 and the bottom of the sample cup 12 to prevent an electrical connection between the thermocouple wires 30, 32 through the gases of combustion emitting from the body of the sample cup 12.

Again, the above-described embodiment of the sample cup 12 is for illustrative purposes only. The blob of the present invention, as described in detail below, may be utilized in any one of a wide variety of different commercially available cups used as sample cups phase change detection devices.

Specifically, in one embodiment of the present invention, a blob 40 is positioned within and preferably attached to the cavity 18 of the sample cup 12. The blob 40 is essentially a mass of material which is positioned within the cavity 18. In one embodiment, the blob 40 is preferably adhered to at least one interior wall of sample cup 12, and more preferably to a top side of the bottom wall 16 of the sample cup 12, by action of the binder component of the blob 40.

The blob 40 according to the invention comprises two essential components: a carbide stabilizing element and a hydrogen source. The blob 40 may also optionally comprise a retardant, a binder and/or a dispersant. The properties and role of each of these components is described hereinafter in greater detail. The blob 40 is preferably essentially devoid of any hygroscopic materials, as such materials have an affinity for atmospheric moisture and thus tend to become damp when exposed to moist air and humid environments.

In one embodiment, the blob 40 is formed by mixing the components of the blob 40 together, depositing the resulting fluid blob mixture with conventional fluid dispensing equipment into the cavity 18 of the sample cup 12, and then drying the fluid blob mixture to obtain the blob 40.

The volume of the fluid blob mixture is preferably 1.89% to 2.70% of the volume of the molten iron or molten cast iron sample contained in the cavity 18 of the sample cup 12. More preferably, the volume of the fluid blob mixture is 2.00% to 2.30% of the volume of the molten iron or molten cast iron sample. Most preferably, the volume of the fluid blob mixture is approximately 2.25% of the volume of the molten iron or molten cast iron sample. The weight of the fluid blob mixture is preferably 0.50% to 0.85% of the weight of the molten iron or molten cast iron sample. More preferably, the weight of the fluid blob mixture is 0.60% to 0.80% of the weight of the molten iron or molten cast iron sample. Most preferably, the weight of the fluid blob mixture is approximately 0.80% of the weight of the molten iron or molten cast iron sample For example, for a sample cup 12 having a cavity volume of 37 milliliters, if the cavity 18 is completely filled by a sample of molten iron or molten cast iron, the weight of the molten metal sample is 270 grams. For such a sample cup 12, assuming that the cavity 18 will be completely filled with a sample of molten iron or molten cast iron, the volume of the fluid blob mixture to be dispensed in the cavity 18 is preferably between 0.7 milliliters and 1 milliliter and the weight of the fluid blob mixture is preferably between 1.5 and 1.7 grams. More preferably, again assuming the cavity 18 will be completely filled with a sample of molten iron or molten cast iron, the volume and weight of the fluid blob mixture are approximately 0.85 milliliters and approximately 1.58 grams, respectively.

After drying, the weight of the blob 40 is preferably 0.35% to 0.45% of the weight of the molten iron or molten cast iron sample. More preferably, the weight of the blob 40 is approximately 0.40% of the weight of the molten iron or molten cast iron sample.

It will be understood by those skilled in the art that the description of a sample cup with a cavity volume of 37 milliliters is for illustrative purposes only. Sample cups having other cavity volumes may be utilized, and thus the blob may be used with molten metal samples of various weights and volumes. As such, it will be understood that, depending on the sample cup being used, the weight and volume of the fluid blob mixture (and thus the volume and weight of the blob 40) will be adjusted accordingly in order to maintain the desired volume and weight percents.

Each component of the blob 40 will now be described in more detail. It will be understood that the phrase "wet weight," as used hereinafter, refers to a state of the blob 40 prior to drying, in which the blob exists as a fluid blob mixture. It will also be understood that the phrase "dry weight," as used hereinafter, refers to a state of the blob 40 after drying of the fluid blob mixture to form a solid, dried blob.

The carbide stabilizing element or carbide stabilizer promotes carbide formation (i.e., white solidification) of the molten iron sample contained in the cavity 18 of the sample cup 12. More particularly, the carbide stabilizer is a metallic material which prevents the precipitation of graphite in the solidifying sample. Upon contact with the molten iron, the blob 40 reacts with the molten iron sample and the carbide stabilizer is released from the blob 40 into the molten iron sample. The carbide stabilizer may preferably be any one of bismuth, boron, tellurium, selenium or compounds or alloys of these elements. Most preferably, the carbide stabilizer is tellurium.

In a preferred embodiment, the carbide stabilizer is present in the form of a powder having an average particle size of 5 to 100 μm. More preferably, the carbide stabilizer is present in the form of a powder having an average particle size of 15 to 50 μm. Most preferably, the carbide stabilizer is present in the form of a powder having an average particle size of approximately 20 μm. Unless otherwise indicated herein, all particle sizes stated herein are $d_{50}$ particle diameters measured by a laser diffraction analyzer or a sedigraph which determines particle size by sedimentation analysis. As well understood by those in the art, the $d_{50}$ diameter represents the size at which half of the individual particles (by weight) are smaller than the specified diameter.

The carbide stabilizer is preferably present in an amount of 5% to 25% by weight based on the total wet weight of the fluid blob mixture and in an amount of 7% to 37% by weight based on the total dry weight of the blob 40. More preferably, the carbide stabilizer is present in an amount of 10% to 20% by weight based on the total wet weight of the fluid blob mixture and in an amount of 15% to 25% by weight based on the total dry weight of the blob 40. Most preferably, the carbide stabilizer is present in an amount of 12% to 14% by weight based on the total wet weight of the fluid blob mixture and in an amount of 18% to 20% by weight based on the total dry weight of the blob 40.

The hydrogen source (i.e., hydrogen releasing material) is a material which evolves into or releases hydrogen to the molten metal, when the blob 40 is contacted by and reacts with the sample of molten metal, particularly molten iron, contained in the sample cup 12.

The hydrogen releasing material is preferably a material having one or more ionic bonded hydroxide groups, as such a material is resistant to moisture gains and losses and, thus, will maintain its level of hydration in moist or dry transport, storage and use conditions or environments. More preferably, the hydrogen releasing material is one that does not absorb moisture. The hydrogen releasing material is also preferably a material which is stable at the drying temperature for the blob 40, but which decomposes at the temperature of use of the detection device 10.

Preferably, the hydrogen releasing material is a hydroxide of an alkaline earth metal. More preferably, the hydrogen releasing material is one of magnesium hydroxide, tellurium hydroxide, calcium hydroxide, and bismuth hydroxide. Most preferably, the hydrogen releasing material is magnesium hydroxide. As such, upon contact and reaction of the blob 40 with the molten iron sample, magnesium is released from the magnesium hydroxide into the molten iron sample.

Magnesium would conventionally not have been used in a detection device designed to promote white iron solidification, because the melting temperature of magnesium is below that of the molten iron, and thus would be expected to alloy into the molten iron and interfere with and counteract the action of the carbide stabilizing element (e.g., tellurium). However, the present inventors have discovered that magnesium can surprisingly be used in a detection device for white iron solidification, because when the magnesium is in the presence of an oxygen containing material that will decompose, releasing an equal or greater stoichiometric proportion of oxygen, the released magnesium is completely neutralized by oxidation prior to any contamination of the molten metal or interference with the tellurium.

The hydrogen releasing material is preferably present in an amount of 10% to 37% by weight based on the total wet weight of the fluid blob mixture and in an amount of 15% to 54% by weight based on the total dry weight of the blob 40. More preferably, the hydrogen releasing material is present in an amount of 12% to 25% by weight based on the total wet weight of the fluid blob mixture and in an amount of 20% to 30% by weight based on the total dry weight of the blob 40. Most preferably, the hydrogen releasing material is present in an amount of 16% to 18% by weight based on the total wet weight of the fluid blob mixture and in an amount of 23% to 25% by weight based on the total dry weight of the blob 40.

In preferred embodiments, the blob 40 also includes a retardant. The retardant is a filler material added to the blob 40 to provide a sufficiently bonded mass that remains substantially intact during solidification of the molten metal sample, such that release of the carbide stabilizer and the release of hydrogen from the hydrogen releasing material (both in vapor form) are delayed upon contact of the blob 40 with the sampled molten metal. More particularly, the retardant is a material which resists reaction and total decomposition of the blob 40 upon contact with the sampled molten metal. Preferably, the retardant is a non-hydrating and refractory (e.g., ceramic) filler material. Preferred examples of the retardant include silica, calcium silicate, magnesium silicate, zirconia, alumina, and compounds thereof. More preferably, the retardant is an alumina silicate, and most preferably, calcined kaolin.

The retardant is preferably present in an amount of 18% to 48% by weight based on the total wet weight of the fluid blob mixture and in an amount of 27% to 71% by weight based on the total dry weight of the blob 40. More preferably, the retardant is present in an amount of 30% to 40% by weight based on the total wet weight of the fluid blob mixture and in an amount of 50% to 60% by weight based on the total dry weight of the blob 40. Most preferably, the retardant is present in an amount of 37% to 39% by weight based on the total wet weight of the fluid blob mixture and in an amount of 54% to 56% by weight based on the total dry weight of the blob 40.

In preferred embodiments, the blob 40 also includes a binder suited for high temperature applications. Preferably, the binder is a thermosetting binder. More preferably, the binder is a non-hygroscopic and non-formaldehyde thermoplastic binder. In one embodiment, the binder is a solution comprising water and a polymerized material, such as polyvinyl alcohol, polyvinyl acetate, polyvinyl butyral and other polyvinyl resins, polystyrene resins, acrylic and methacrylic acid ester resins, polyisobutylene, polyamides and silicones. Most preferably, the binder comprises a partially hydrolyzed polyvinyl alcohol solution.

The binder is preferably present in an amount of 27% to 37% by weight based on the total wet weight of the fluid blob mixture and in an amount of 1% to 4% by weight based on the total dry weight of the blob 40. More preferably, the binder is present in an amount of 30% to 35% by weight based on the total wet weight of the fluid blob mixture and in an amount of 1% to 3% by weight based on the total dry weight of the blob 40. Most preferably, the binder is present in an amount of 31% to 33% by weight based on the total wet weight of the fluid blob mixture and in an amount of 1.5% to 2.5% by weight based on the total dry weight of the blob 40.

In preferred embodiments, the blob 40 also includes a dispersant. The dispersant is a material which maintains the dispersed particles of the various components in suspension to prevent settling of these particles. Thus, while the inclusion of a dispersant is not necessary, doing so has been found to be beneficial for manufacturing of the blob 40 on a commercial scale. Preferred examples of the dispersant include trisodium citrate, ammonium citrate and like materials having similar properties thereto. Most preferably, the dispersant is trisodium citrate.

The dispersant is preferably present in an amount of 0.04% to 1.3% by weight based on the total wet weight of the fluid blob mixture and in an amount of 0.06% to 2% by weight based on the total dry weight of the blob 40. More preferably, the dispersant is present in an amount of 0.08% to 1% by weight based on the total wet weight of the fluid blob mixture and in an amount of 0.1% to 1% by weight based on the total dry weight of the blob 40. Most preferably, the dispersant is present in an amount of 0.1% to 0.5% by weight based on the total wet weight of the fluid blob mixture and in an amount of 0.3% to 0.5% by weight based on the total dry weight of the blob 40.

As discussed above, in one embodiment, the weight of the fluid blob mixture is preferably 0.80% of the weight a molten iron/molten cast iron sample that would be contained in the sample cup 12 and the weight of the blob 40 is preferably 0.40% of the weight the molten iron/molten cast iron sample. As such, the weight percentages of the components of the fluid blob mixture and the blob 40 as compared with the total weight of the molten iron/molten cast iron sample are preferably as shown in Table 1 below:

TABLE 1

| Blob Formulation | | |
|---|---|---|
| | wt % of molten metal sample | |
| Component | Fluid Blob Mixture | Blob 40 |
| Carbide stabilizer | 0.96%-1.12% | 0.72%-0.80% |
| Hydrogen source | 1.28%-1.44% | 0.92%-1.0% |
| Retardant | 2.96%-3.12% | 2.16%-2.24% |
| Binder | 2.48%-2.64% | 0.06%-0.10% |
| Dispersant | 0.01%-0.04% | 0.01%-0.02% |

In another embodiment, the blob 40 is formed by dry compression. Specifically, the components of the blob 40 are mixed together and then co-pressed into a pellet-like blob which is attached or adhered within the cavity 18 of the sample cup 12 by the use of an adhesive or refractory cement. Alternatively, the blob may be positioned within a recess formed in a wall of the sample cup.

In such an embodiment, the pressing achieves a mechanical interlocking of the particles of the carbide stabilizer and hydrogen releasing material. As such, a binder and dispersant are not necessary. In addition, the retardant component may be eliminated, such that release of the carbide stabilizer and hydrogen occurs relatively quickly. The carbide stabilizer is preferably present in the blob 40 in an amount of 15% to 60% by weight and the hydrogen releasing material is preferably present in the blob 40 in an amount of 40% to 85% based on the total weight of the blob. More preferably, the carbide stabilizer is present in an amount of 25% to 55% by weight and the hydrogen releasing material is present in an amount of 45% to 75% based on the total weight of the blob. Most preferably, the carbide stabilizer is present in an amount of 30% to 35% by weight and the hydrogen releasing material is present in an amount of 65% to 70% based on the total weight of the blob.

Also, in such an embodiment, the weight of the carbide stabilizer preferably constitutes 0.05% to 0.10%, and more preferably constitutes 0.07% to 0.095%, of the weight of a molten iron sample that would be contained in the sample cup 12. Most preferably, the weight of the carbide stabilizer constitutes approximately 0.074% of the weight of the molten iron sample. The weight of the hydrogen releasing material preferably constitutes 0.11% to 0.22%, and more preferably constitutes 0.13% to 0.19%, of the weight of the molten iron sample. Most preferably, the weight of the hydrogen releasing material constitutes approximately 0.14% to 0.17% of the weight of the molten iron sample.

In another embodiment, the blob 40 comprises only one essential component, namely tellurium hydroxide as a hydrogen source or hydrogen releasing material. As such, upon contact and reaction of the blob 40 with the molten iron sample, tellurium (a carbide stabilizing element), oxygen and hydrogen are all released from the tellurium hydroxide into the molten iron sample. Preferably, the weight of the tellurium hydroxide constitutes 0.120% to 0.175% of the weight of the molten iron sample. More preferably, the weight of the tellurium hydroxide constitutes approximately 0.150% of the weight of the molten iron sample.

The formation of various blobs 40 in accordance with preferred embodiments of the present invention will now be described in more detail with reference to the following specific, non-limiting examples:

EXAMPLES

Five exemplary different blob mixtures were prepared by mixing various materials in the proportions shown in Tables 2-6 below:

TABLE 2

Blob A Formulation

| Blob Component | wt % (wet) | wt % (dry) |
|---|---|---|
| Carbide stabilizer | 12.7% | 18.4% |
| Hydrogen source | 16.8% | 24.4% |
| Retardant | 37.9% | 54.9% |
| Binder | 32.3% | 1.9% |
| Dispersant | 0.3% | 0.4% |

TABLE 3

Blob B Formulation

| Blob Component | wt % (wet) | wt % (dry) |
|---|---|---|
| Carbide stabilizer | 13.0% | 18.4% |
| Hydrogen source | 17.0% | 24.4% |
| Retardant | 38.0% | 55.3% |
| Binder | 32.0% | 1.9% |
| Dispersant | — | — |

TABLE 4

Blob C Formulation

| Blob Component | wt % (dry) |
|---|---|
| Carbide stabilizer | 33.3% |
| Hydrogen source | 66.7% |
| Retardant | — |
| Binder | — |
| Dispersant | — |

TABLE 5

Blob D Formulation

| Blob Component | wt % (dry) |
|---|---|
| Carbide stabilizer | 30.9% |
| Hydrogen source | 69.1% |
| Retardant | — |
| Binder | — |
| Dispersant | — |

TABLE 6

Blob E Formulation

| Blob Component | wt % (dry) |
|---|---|
| Carbide stabilizer | — |
| Hydrogen source | 100% |
| Retardant | — |
| Binder | — |
| Dispersant | — |

The carbide stabilizer for Blobs A, B and C was tellurium. The hydrogen source for Blobs A, B and C was magnesium hydroxide. The hydrogen source of Blob D was calcium hydroxide. The hydrogen source of Blob E was tellurium hydroxide. The retardant for Blobs A and B was calcined kaolin. The binder for Blobs A and B was 3% polyvinyl alcohol-water solution. The dispersant for Blob A was trisodium citrate.

For Blobs A and B, the respective components of the blobs were mixed together to form fluid blob mixtures. Each prepared fluid blob mixture was then dispensed into the cavity of a molten metal sample cup (i.e., sample cup 12 as described above). The sample cup had a casting modulus of approximately 6 centimeters and a volume of approximately 37 milliliters. The volume and weight of the dispensed fluid blob mixture were approximately 0.85 milliliters and approximately 2.16 grams, respectively.

The sample cup with the dispensed fluid blob mixture therein was then allowed to dry in ambient conditions to form a solid, dried blob 40 and to effect a final cure of the binder, which in turn adheres or bonds the dried blob 40 within the cavity 18 of the sample cup 12. The weight of the resulting solid, dried blob 40 was approximately 0.4% of the weight of the molten iron sample to be contained in the sample cup 12, assuming the sample cup cavity were completely filled.

For Blobs C and D, the components of the blob were mixed together and subsequently co-pressed to form a pellet-like Blobs C and D. For Blob E, the particles of the tellurium hydroxide were pressed together to form pellet-like Blob E. Each of the Blobs C, D and E was then attached or adhered within the cavity of a sample cup by a refractory cement. The sample cup had a casting modulus of approximately 6 centimeters and a volume of approximately 37 milliliters.

Each of Blobs A, B, C, D and E disposed within the cavity of a respective sample cup, was then contacted with a molten iron sample. For each of Blobs A, B, C, D and E, the weight percentages of the respective components relative to the weight of the molten iron sample are shown in Table 7 below:

TABLE 7

Weight Percents of Blob Components

| Component | Blob A | Blob B | Blob C | Blob D | Blob E |
|---|---|---|---|---|---|
| Carbide stabilizer | 0.074% | 0.074% | 0.091% | 0.091% | — |
| Hydrogen source | 0.098% | 0.098% | 0.182% | 0.205% | 0.15% |
| Retardant | 0.220% | 0.221% | — | — | — |
| Binder | 0.008% | 0.008% | — | — | — |
| Dispersant | 0.002% | — | — | — | — |

For Blob A, in particular, the presence of the magnesium hydroxide was found to enable cross-linking of the polyvinyl alcohol of the binder without the application of any heat treatment. While polyvinyl alcohol would typically tend to absorb ambient moisture (and thus not be suitable for purposes of the present invention), cross-linked polyvinyl alcohol exhibits sufficient moisture-resistant properties as necessary for the blob 40. Thus, a blob having superior moisture-resistant properties was surprisingly found to result from the particular combination of magnesium hydroxide and polyvinyl alcohol.

In addition, for each of the Blobs A, B and C, both hydrogen (released from the magnesium hydroxide) and tellurium were released into the molten iron sample. In addition, the magnesium released from the magnesium hydroxide was surprisingly found to be completely neutralized upon reaction of the blob 40 with the molten iron sample. As such, the released magnesium did not have any contaminating effects on the molten iron or interfere with the tellurium. Instead, the released magnesium surprisingly permitted a complete white solidification of the molten iron.

Also, each of the Blobs A, B, C, D and E was found to be resistant to changes in hydration levels. Specifically, each of the Blobs A, B, C, D and E was resistant to moisture gain and moisture loss during long-term transport and/or storage, even in extremely humid or extremely dry transport and storage conditions.

Accordingly, either no environmentally absorbed water accumulated on the Blobs A, B, C, D and E, or any such accumulation was minimal. As a result, when each of the Blobs A, B, C, D and E was exposed to the molten metal sample, any uncontrolled boiling was eliminated or minimal. Thus, the amount of molten metal initially poured into the sample cup remained virtually unchanged during solidification of the metal. As a result, use of the Blobs A, B, C, D and E resulted in predictable cooling/solidification times from pour to pour.

Also, each of the Blobs A, B, C, D and E did not contain any trapped moisture, and thus was not subject to premature drying typically effected due to such moisture. Thus, the composition of each blob, and specifically the content of the hydrogen releasing material, remains virtually unchanged from the point of manufacture, through transport and storage, until use.

Further, the amount of carbide stabilizer, particularly tellurium, needed to achieve complete white solidification in the blob 40 is much less as compared with prior art coatings and blobs, as shown in Table 8 below:

TABLE 8

| | Tellurium Content | | |
|---|---|---|---|
| | Te wt | Fe wt (theoretical fill)* | % Te (theoretical fill) |
| Prior Art Blob | 0.388 | 343.0 | 0.113% |
| Blob 40 | 0.200 | 269.4 | 0.074% |

*The "theoretical" values refer to a state in which the volume of the sample cup 12 is completely filled with molten iron.

Thus, blobs of the present invention and detection devices including blobs of the present invention may be used over a broad range of pouring temperatures, pouring conditions, and storage and transport conditions with excellent results.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A detection device for molten metal, the device comprising:
    a sample cup having a cavity configured to receive a sample of molten metal and allow the sample of molten metal to solidify therein in a white structure;
    a blob arranged in the cavity and configured to contact the sample of molten metal as it solidifies within the cavity, the blob comprising tellurium as a carbide stabilizing element, magnesium hydroxide as a hydrogen releasing material and a 3% polyvinyl alcohol-water solution as a binder; and
    a temperature sensor.

2. The detection device according to claim 1, wherein the blob comprises 0.35% to 0.45% by weight based on a total weight of a sample of molten metal.

3. The detection device according to claim 1, wherein the blob is resistant to changes in its hydration level during transport and storage of the blob.

4. The detection device according to claim 1, wherein the blob further comprises a retardant which resists reaction of the blob upon contact with molten metal.

5. The detection device according to claim 1, wherein the carbide stabilizing element comprises 7% to 37% by weight based on a total weight of the blob.

6. The detection device according to claim 1, wherein the magnesium hydroxide comprises 15% to 54% by weight based on a total weight of the blob.

7. The detection device according to claim 1, wherein the 3% polyvinyl alcohol-water solution comprises 1% to 4% by weight based on a total weight of the blob.

8. The detection device according to claim 1, wherein the blob comprises tellurium in an amount of 15% to 60% by weight based on a total weight of the blob and magnesium hydroxide in an amount of 40% to 85% by weight based on the total weight of the blob, the blob being resistant to moisture gain and moisture loss during transport and storage.

9. The detection device according to claim 8, wherein the tellurium is present in an amount of 0.05% to 0.10% by weight based on a total weight of a molten iron sample and the magnesium hydroxide is present in an amount of 0.11% to 0.22% by weight based on the total weight of the molten iron sample.

* * * * *